US009314168B2

(12) United States Patent
Watson et al.

(10) Patent No.: US 9,314,168 B2
(45) Date of Patent: Apr. 19, 2016

(54) DETECTING SLEEP EVENTS USING LOCALIZED BLOOD PRESSURE CHANGES

(75) Inventors: James Nicholas Watson, Dunfermline (GB); Rakesh Sethi, Vancouver (CA); Paul Stanley Addison, Edinburgh (GB)

(73) Assignee: Nellcor Puritan Bennett Ireland, Mervue, Galway (IE)

( * ) Notice: Subject to any disclaimer, the term of this patent is extended or adjusted under 35 U.S.C. 154(b) by 1737 days.

(21) Appl. No.: 12/242,719

(22) Filed: Sep. 30, 2008

(65) Prior Publication Data

US 2010/0081943 A1 Apr. 1, 2010

(51) Int. Cl.
*A61B 5/00* (2006.01)
*A61B 5/021* (2006.01)

(52) U.S. Cl.
CPC .............. *A61B 5/021* (2013.01); *A61B 5/0059* (2013.01); *A61B 5/4809* (2013.01); *A61B 5/4812* (2013.01); *A61B 5/6816* (2013.01); *A61B 5/6826* (2013.01); *A61B 5/6829* (2013.01); *A61B 5/6838* (2013.01)

(58) Field of Classification Search
CPC .. A61B 5/4809; A61B 5/0059; A61B 5/4818; G06F 19/345
See application file for complete search history.

(56) References Cited

U.S. PATENT DOCUMENTS

| | | |
|---|---|---|
| 3,835,840 A | 9/1974 | Mount |
| 4,561,447 A | 12/1985 | Kawamura et al. |
| 4,676,253 A | 6/1987 | Newman |
| 4,729,382 A | 3/1988 | Schaffer |
| 4,830,017 A | 5/1989 | Perry |
| 4,836,213 A | 6/1989 | Wenzel et al. |
| 4,854,327 A | 8/1989 | Kunig |
| 4,898,176 A | 2/1990 | Petre |
| 4,924,871 A | 5/1990 | Honeyager |
| 4,928,700 A | 5/1990 | Harada |
| 4,951,679 A | 8/1990 | Harada |
| 4,976,268 A | 12/1990 | Kurosawa et al. |
| 4,987,900 A | 1/1991 | Eckerle |
| 5,065,765 A | 11/1991 | Eckerle |
| 5,103,831 A | 4/1992 | Niwa |
| 5,105,815 A | 4/1992 | Hall et al. |
| 5,119,824 A | 6/1992 | Niwa |
| 5,131,400 A | 7/1992 | Harada |
| 5,163,328 A | 11/1992 | Holland |
| 5,170,796 A | 12/1992 | Kobayashi |
| 5,176,143 A | 1/1993 | Eckerle et al. |
| 5,178,154 A | 1/1993 | Ackmann et al. |
| 5,179,956 A | 1/1993 | Harada et al. |
| 5,204,922 A | 4/1993 | Weir |
| 5,238,000 A | 8/1993 | Niwa |
| 5,241,964 A | 9/1993 | McQuilkin |
| 5,255,686 A | 10/1993 | Takeda et al. |
| 5,269,312 A | 12/1993 | Kawamura et al. |
| 5,289,823 A | 3/1994 | Eckerle |
| 5,309,917 A | 5/1994 | Wang |
| 5,431,159 A | 7/1995 | Baker |
| 5,450,852 A | 9/1995 | Archibald et al. |
| 5,467,771 A | 11/1995 | Narimatsu |
| 5,490,506 A | 2/1996 | Takatani |
| 5,494,043 A | 2/1996 | O'Sullivan et al. |
| 5,497,779 A | 3/1996 | Takaya |
| 5,505,209 A | 4/1996 | Reining |
| 5,533,511 A | 7/1996 | Kaspari |
| 5,535,753 A | 7/1996 | Petrucelli et al. |
| 5,562,621 A | 10/1996 | Claude et al. |
| 5,564,427 A | 10/1996 | Aso et al. |
| 5,575,284 A | 11/1996 | Athan |
| 5,617,868 A | 4/1997 | Harada |
| 5,640,964 A | 6/1997 | Archibald et al. |
| 5,649,542 A | 7/1997 | Archibald et al. |
| 5,649,543 A | 7/1997 | Hosaka et al. |
| 5,676,140 A | 10/1997 | Ukawa |
| 5,682,898 A | 11/1997 | Aung |
| 5,685,316 A | 11/1997 | Schookin et al. |
| 5,704,362 A | 1/1998 | Hersh et al. |
| 5,709,212 A | 1/1998 | Sugo |
| 5,720,292 A | 2/1998 | Poliac |
| 5,722,414 A | 3/1998 | Archibald et al. |
| 5,738,103 A | 4/1998 | Poliac |
| 5,743,856 A | 4/1998 | Oka et al. |
| 5,755,669 A | 5/1998 | Ono et al. |
| 5,762,610 A | 6/1998 | Narimatsu |
| 5,772,601 A | 6/1998 | Oka |
| 5,772,602 A | 6/1998 | Sakai |
| 5,776,071 A | 7/1998 | Inukai |

(Continued)

FOREIGN PATENT DOCUMENTS

| | | |
|---|---|---|
| EP | 0443267 | 8/1991 |
| EP | 0755221 | 1/1997 |

(Continued)

OTHER PUBLICATIONS

Leroy, et al. Hypertension (1996) 28:6, pp. 937-943.*
Imholz et al. (Cardio. Res., 1998, vol. 38, pp. 605-616).*
Avolio (Journal of Hypertension, 2002, vol. 20, pp. 2341-2343).*
Bank, Alan J., Kaiser, Daniel R., "Smooth Muscle Relaxation: Effects on Arterial Compliance, Distensibility, Elastic Modulus, and Pulse Wave Velocity," Hypertension, vol. 32, No. 2, Aug. 1998, pp. 356-359.
Berne, Robert M., Levy, Matthew N., eds., Physiology, 2nd edition, St. Louis, The C.V. Mosby Co., 1988, pp. 357-681.
Finkelstein, Stanley M., Cohn, Jay N., "First- and Third-Order Models for Determining Arterial Compliance," Journal of Hypertension, vol. 10, supplement 6, Aug. 1992, pp. S11-S14.
Fitchett, D., Bouthier, JD, Simon, A. Ch., Levenson, JA, Safar, ME, "Forearm Arterial Compliance: The Validation of a Plethysmographic Technique for the Measurement of Arterial Compliance," Clinical Science, vol. 67, No. 1, Jul. 1984, pp. 69-72.

(Continued)

*Primary Examiner* — J. E. Angell
(74) *Attorney, Agent, or Firm* — Shvarts & Leiz LLP

(57) ABSTRACT

Techniques for detecting sleep events are disclosed. In some embodiments, a continuous non-invasive blood pressure ("CNIBP") monitoring system may be used to obtain blood pressure values from a subject during a sleep study. Changes in the blood pressure over time may be determined and analyzed in order to identify a sleep event. The localized blood pressure changes may be interpreted in isolation or in combination with other signals collected from the subject.

17 Claims, 7 Drawing Sheets

(56) References Cited

U.S. PATENT DOCUMENTS

| | | |
|---|---|---|
| 5,785,659 A | 7/1998 | Caro et al. |
| 5,791,347 A | 8/1998 | Flaherty et al. |
| 5,797,395 A | 8/1998 | Martin |
| 5,797,850 A | 8/1998 | Archibald et al. |
| 5,810,736 A | 9/1998 | Pail |
| 5,827,181 A | 10/1998 | Dias |
| 5,830,131 A | 11/1998 | Caro et al. |
| 5,832,924 A | 11/1998 | Archibald et al. |
| 5,833,618 A | 11/1998 | Caro |
| 5,848,970 A | 12/1998 | Voss |
| 5,857,975 A | 1/1999 | Golub |
| 5,873,834 A | 2/1999 | Yanagi et al. |
| 5,891,023 A | 4/1999 | Lynn |
| 5,904,654 A | 5/1999 | Wohltmann et al. |
| 5,924,979 A | 7/1999 | Swedlow et al. |
| 5,941,828 A | 8/1999 | Archibald et al. |
| 5,964,711 A | 10/1999 | Voss |
| 6,002,952 A | 12/1999 | Diab |
| 6,004,274 A | 12/1999 | Nolan |
| 6,007,492 A | 12/1999 | Goto et al. |
| 6,011,986 A | 1/2000 | Diab et al. |
| 6,022,320 A | 2/2000 | Ogura |
| 6,027,452 A | 2/2000 | Flaherty et al. |
| 6,027,453 A | 2/2000 | Miwa |
| 6,027,455 A | 2/2000 | Inukai et al. |
| 6,045,509 A | 4/2000 | Caro et al. |
| 6,067,462 A | 5/2000 | Diab |
| 6,083,171 A | 7/2000 | Ono et al. |
| 6,095,987 A | 8/2000 | Shmulewitz |
| 6,135,966 A | 10/2000 | Ko |
| 6,157,850 A | 12/2000 | Diab et al. |
| 6,159,157 A | 12/2000 | Archibald et al. |
| 6,161,038 A | 12/2000 | Schookin et al. |
| 6,186,954 B1 | 2/2001 | Narimatsu |
| 6,186,955 B1 | 2/2001 | Baura |
| 6,190,382 B1 | 2/2001 | Ormsby et al. |
| 6,196,974 B1 | 3/2001 | Miwa |
| 6,217,524 B1 | 4/2001 | Orr et al. |
| 6,227,196 B1 | 5/2001 | Jaffe et al. |
| 6,228,034 B1 | 5/2001 | Voss et al. |
| 6,241,661 B1 | 6/2001 | Schluess et al. |
| 6,241,679 B1 | 6/2001 | Curran |
| 6,245,022 B1 | 6/2001 | Archibald et al. |
| 6,251,081 B1 | 6/2001 | Narimatsu |
| 6,263,222 B1 | 7/2001 | Diab et al. |
| 6,292,689 B1 | 9/2001 | Wallace |
| 6,293,915 B1 | 9/2001 | Amano et al. |
| 6,299,582 B1 | 10/2001 | Brockway et al. |
| 6,332,867 B1 | 12/2001 | Chen et al. |
| 6,350,242 B1 | 2/2002 | Doten et al. |
| 6,371,921 B1 | 4/2002 | Caro |
| 6,443,905 B1 | 9/2002 | Nissila et al. |
| 6,463,311 B1 | 10/2002 | Diab |
| 6,471,646 B1 | 10/2002 | Thede |
| 6,471,655 B1 | 10/2002 | Baura |
| 6,506,161 B2 | 1/2003 | Brockway et al. |
| 6,514,211 B1 | 2/2003 | Baura |
| 6,524,240 B1 | 2/2003 | Thede |
| 6,561,986 B2 | 5/2003 | Baura |
| 6,589,185 B1 | 7/2003 | Archibald et al. |
| 6,599,251 B2 | 7/2003 | Chen et al. |
| 6,602,199 B2 | 8/2003 | Chen et al. |
| 6,602,201 B1 | 8/2003 | Hepp et al. |
| 6,606,511 B1 | 8/2003 | Ali et al. |
| 6,626,839 B2 | 9/2003 | Doten et al. |
| 6,631,281 B1 | 10/2003 | Kastle |
| 6,645,156 B2 | 11/2003 | Oka |
| 6,658,277 B2 | 12/2003 | Wasserman |
| 6,684,090 B2 | 1/2004 | Ali et al. |
| RE38,476 E | 3/2004 | Diab et al. |
| 6,699,194 B1 | 3/2004 | Diab |
| 6,767,328 B2 | 7/2004 | Kulik |
| 6,773,397 B2 | 8/2004 | Kelly |
| 6,783,498 B2 | 8/2004 | Sackner |
| 6,811,538 B2 | 11/2004 | Westbrook et al. |
| 6,816,741 B2 | 11/2004 | Diab |
| 6,822,564 B2 | 11/2004 | Al-Ali |
| 6,826,419 B2 | 11/2004 | Diab |
| 6,827,688 B2 | 12/2004 | Goto et al. |
| 6,852,083 B2 | 2/2005 | Caro |
| 6,855,112 B2 | 2/2005 | Kao |
| 6,863,652 B2 | 3/2005 | Huang et al. |
| 6,869,403 B2 | 3/2005 | Narimatsu et al. |
| 6,882,874 B2 | 4/2005 | Huiku |
| 6,929,610 B2 | 8/2005 | Forstner |
| 6,996,427 B2 | 2/2006 | Ali et al. |
| 7,004,907 B2 | 2/2006 | Banet |
| 7,043,293 B1 | 5/2006 | Baura |
| 7,044,918 B2 | 5/2006 | Diab |
| 7,070,566 B2 | 7/2006 | Medero et al. |
| 7,074,192 B2 | 7/2006 | Friedman et al. |
| 7,079,035 B2 | 7/2006 | Bock et al. |
| 7,087,025 B2 | 8/2006 | Baruch |
| 7,142,901 B2 | 11/2006 | Kiani et al. |
| 7,184,809 B1 | 2/2007 | Sterling |
| 7,215,984 B2 | 5/2007 | Diab et al. |
| 7,215,986 B2 | 5/2007 | Diab et al. |
| 7,252,636 B2 | 8/2007 | Brown |
| 7,274,955 B2 | 9/2007 | Kiani et al. |
| 7,297,119 B2 | 11/2007 | Westbrook et al. |
| 7,309,314 B2 | 12/2007 | Grant et al. |
| 7,320,030 B2 | 1/2008 | Brown |
| 7,335,162 B2 | 2/2008 | Eide |
| 7,376,238 B1 | 5/2008 | Rivas et al. |
| 7,387,608 B2 | 6/2008 | Dunlop et al. |
| 7,390,300 B2 | 6/2008 | Inukai |
| 7,390,301 B2 | 6/2008 | Skrabal |
| 7,393,327 B2 | 7/2008 | Inukai |
| 7,400,257 B2 | 7/2008 | Rivas |
| 7,455,643 B1 | 11/2008 | Li et al. |
| 7,481,772 B2 | 1/2009 | Banet |
| 7,485,095 B2 | 2/2009 | Shusterman |
| 2005/0027207 A1 | 2/2005 | Westbrook et al. |
| 2005/0148885 A1 | 7/2005 | Tweed et al. |
| 2005/0222502 A1 | 10/2005 | Cooper |
| 2005/0222503 A1 | 10/2005 | Dunlop et al. |
| 2005/0250998 A1 | 11/2005 | Huiku |
| 2005/0251344 A1 | 11/2005 | Appel et al. |
| 2005/0261594 A1 | 11/2005 | Banet |
| 2006/0009700 A1 | 1/2006 | Brumfield et al. |
| 2006/0063992 A1 | 3/2006 | Yu et al. |
| 2006/0063993 A1 | 3/2006 | Yu et al. |
| 2006/0074322 A1 | 4/2006 | Nitzan |
| 2006/0079945 A1 | 4/2006 | Libbus |
| 2006/0206021 A1 | 9/2006 | Diab |
| 2006/0217614 A1 | 9/2006 | Takala et al. |
| 2006/0217628 A1 | 9/2006 | Huiku |
| 2006/0241506 A1 | 10/2006 | Melker et al. |
| 2006/0241975 A1 | 10/2006 | Brown |
| 2006/0285736 A1 | 12/2006 | Brown |
| 2006/0287603 A1 | 12/2006 | Bartnik et al. |
| 2007/0066910 A1 | 3/2007 | Inukai et al. |
| 2007/0083093 A1 | 4/2007 | Diab |
| 2007/0118045 A1 | 5/2007 | Naghavi et al. |
| 2007/0225582 A1 | 9/2007 | Diab et al. |
| 2007/0249467 A1 | 10/2007 | Hong et al. |
| 2007/0276632 A1 | 11/2007 | Banet |
| 2008/0015451 A1 | 1/2008 | Hatib et al. |
| 2008/0030468 A1 | 2/2008 | Ali et al. |
| 2008/0033305 A1 | 2/2008 | Hatib et al. |
| 2008/0081969 A1 | 4/2008 | Feldman et al. |
| 2008/0132798 A1 | 6/2008 | Hong et al. |
| 2008/0190430 A1 | 8/2008 | Melker et al. |
| 2008/0214903 A1 | 9/2008 | Orbach |
| 2008/0214942 A1 | 9/2008 | Oh et al. |
| 2008/0242955 A1 | 10/2008 | Uutela et al. |
| 2009/0048497 A1 | 2/2009 | Keren |

FOREIGN PATENT DOCUMENTS

| | | |
|---|---|---|
| EP | 1259157 | 11/2002 |
| GB | 2 356 250 | 5/2001 |
| GB | 2 356 251 | 5/2001 |
| GB | 2 356 252 | 5/2001 |

(56) References Cited

FOREIGN PATENT DOCUMENTS

| JP | 03-231630 | 10/1991 |
|---|---|---|
| JP | 06-142082 | 5/1994 |
| JP | 07-136136 | 5/1995 |
| JP | 2003-225268 | 8/2003 |
| WO | WO 2008/043864 | 4/2008 |

OTHER PUBLICATIONS

Fletcher, Gerald F., ed., Cardiovascular Response to Exercise, Mt. Kisco, NY, Futura Publishing Co., 1994.

Fung, YC, Biomechanics: Circulation, 2nd Edition, New York, Springer, 1997.

Geddes, LA, Handbook of Blood Pressure Measurement, Clifton, New Jersey, Humana Press, 1991.

Millasseau, Sandrine C, Guigui, Franck G, Kelly, Ronan P., Prasad, Krishna, Cockcroft, John R., Ritter, James M., Chowienczyk, Philip J., Noninvasive Assessment of the Digital Volume Pulse: Comparison with the Peripheral Pressure Pulse, Hypertension, vol. 36, No. 6, Dec. 2000, pp. 952-956.

Moyle, John TB, Hahn, CEW, Adams, Anthony P, Pulse Oximetry, Revised Edition, London, BMJ Books, 1998.

Nara, Andrew R., Burns, Michael P., Downs, W. Gregory, Blood Pressure, Redmond, Washington, SpaceLabs Inc., 1989.

Nichols, Wilmer W., O'Rourke, Michael F., McDonald's Blood Flow in Arteries: Theoretic, Experimental, and Clinical Principles, 3rd Edition, Philadelphia, Lea & Febiger, 1990.

O'Rourke, Michael F., Gallagher, David E., "Pulse Wave Analysis," Journal of Hypertension, vol. 14, supplement 5, Dec. 1996, pp. 5147-5157.

Takazawa, Kenji, Tanaka, Nobuhiro, Fujita, Masami, Matsuoka, Osamu, Saiki, Tokuyu, Aikawa, Masaru, Tamura, Sinobu, Ibukiyama, Chiharu, "Assessment of Vasoactive Agents and Vascular Aging by the Second Derivative of Photoplethysmogram Waveform," Hypertension, vol. 32, No. 2, Aug. 1998, pp. 365-370.

Tardy, Y, Meister, JJ, Perret F, Brunner, HR, Arditi, M, "Non-Invasive Estimate of the Mechanical Properties of Peripheral Arteries from Ultrasonic and Photoplethysmographic Measurements," Clinical Physics and Physiological Measurement, vol. 12, No. 1, pp. 39-54, Feb. 1991.

Young, Christopher C., Mark, Jonathan B., White, William, DeBree, Ashley, Vender, Jeffery S., Fleming, Andrew, "Clinical Evaluation of Continuous Noninvasive Blood Pressure Monitoring: Accuracy and Tracking Capabilities," Journal of Clinical Monitoring, vol. 11, No. 4, Jul. 1995, pp. 245-252.

Davies R J et al: "Identification of Sleep Disruption and Sleep Disordered Breathing from the Systolic Blood Pressure Profile." Thorax Dec. 1993, vol. 48, No. 12, Dec. 1993, pp. 1242-1247, XP002562392 ISSN:0040-6376.

Leroy M et al: "Short-Term Variability of Blood Pressure During Sleep in Snorers With or Without Apnea." Hypertension Dec. 1996, vol. 28, No. 6, Dec. 1996, pp. 937-943, XP009127672 ISSN: 0194-911x.

International Search Report PCT/IB2009/006895, 8 pages, mailed Apr. 14, 2010.

* cited by examiner

DETECTING SLEEP EVENTS USING LOCALIZED BLOOD PRESSURE CHANGES

SUMMARY

The present disclosure relates to blood pressure monitoring and, more particularly, to detecting sleep events using localized blood pressure changes.

Sleep studies generally observe subjects during sleep. Sleep studies may be used to detect sleep problems such as sleep apnea and sleep arousal. Sleep studies may be performed in one's home or at a sleep lab. Various physiological parameters may be observed during a sleep study. However, blood pressure measurements traditionally have not been used in sleep studies.

In some embodiments of the present disclosure, a continuous non-invasive blood pressure ("CNIBP") monitoring system may be used to obtain blood pressure values from a subject during a sleep study. A sensor or probe may be used to obtain at least one photoplethysmograph (PPG) signal from the subject. From the at least one PPG signal, the blood pressure of the subject may be determined. Physiological changes of a subject may cause the determined blood pressure values to be inaccurate. CNIBP monitoring systems are typically calibrated periodically or when certain events occur (e.g., when detected blood pressure values exceed a pre-defined threshold). The calibration process may involve the use of an invasive device (e.g., an occluding cuff) to obtain a reference blood pressure for use in the calibration process. Performing such a calibration during a sleep study, however, may cause the subject to wake up. Accordingly, during a sleep study, the CNIBP monitoring system may be calibrated at the beginning of the study and recalibration may not be performed until after the study is over or after the subject wakes up. By not recalibrating the system during sleep, the blood pressure values over time may diverge from the subject's actual blood pressure. Even if the blood pressure values themselves may become inaccurate, changes in these values may accurately represent changes in the subject's actual blood pressure. Thus, changes in the blood pressure values may be used to accurately detect sleep events.

In some embodiments, a first PPG signal and a second PPG signal may be detected from two locations on a subject. A time difference between a first time and a second time associated with pulses in the first PPG signal and the second PPG signal may be determined and used to compute blood pressure values. In some embodiments, a PPG signal may be detected from a location on a subject, and at least two characteristic points in the PPG signal may be detected. A time difference between two of the at least two characteristic points may be determined and used to calculate blood pressure values. In some embodiments, a PPG signal may be detected from a location on a subject, and locations of pulses in the PPG signal may be determined. An area under a portion of one of the pulses may be measured and used to calculate blood pressure values.

Localized changes in the calculated blood pressure may be determined and analyzed. Based at least in part on the analyzed changes, a sleep event may be identified. In an embodiment a first blood pressure value and a second blood pressure value may be calculated at a first time and a second time respectively. A blood pressure difference between the first and second blood pressure values may be determined and compared to a pre-defined threshold value. A sleep event may be identified if the blood pressure difference is greater than the pre-defined threshold value.

In an embodiment, a long-term blood pressure average and a short-term blood pressure average may be calculated. A blood pressure difference between the long-term and short-term blood pressure averages may be determined and compared to a pre-defined threshold value. A sleep event may be identified if the blood pressure difference is greater than the pre-defined threshold value.

In an embodiment, a first blood pressure value and a second blood pressure value may be calculated at a first time and second time respectively. A counter may be set to zero. A blood pressure difference between the first and second blood pressure values and a time difference between the first and second times may be determined. A ratio of the blood pressure difference to the time difference may be calculated and compared to a first pre-defined threshold value. If the ratio is greater than the first pre-defined threshold value, the counter may be increased by 1 and compared to a second pre-defined threshold value. A sleep event may be identified if the ratio continues to be greater than the first pre-defined threshold value and the counter is incremented to a value that greater than the second pre-defined threshold value.

In an embodiment a first blood pressure value associated with a first time when the blood pressure of the subject begins to change significantly may be detected. A second blood pressure value associated with a second time when the blood pressure stabilizes may also be detected. A time difference between the first and second times, and a blood pressure difference between the first and second blood pressure values may be measured. The time difference and blood pressure difference may be respectively compared to a first pre-defined threshold value and a second pre-defined threshold value. A sleep event may be identified if the time difference is less than the first pre-defined threshold value and the blood pressure difference is greater than the second pre-defined threshold value.

Sleep events may also be identified using a combination of the foregoing embodiments. For example, a sleep event may be identified if 2 or more identification processes indicate that the sleep event should be identified.

BRIEF DESCRIPTION OF THE DRAWINGS

The above and other features of the present disclosure, its nature and various advantages will be more apparent upon consideration of the following detailed description, taken in conjunction with the accompanying drawings in which.

DETAILED DESCRIPTION

Figure 1:
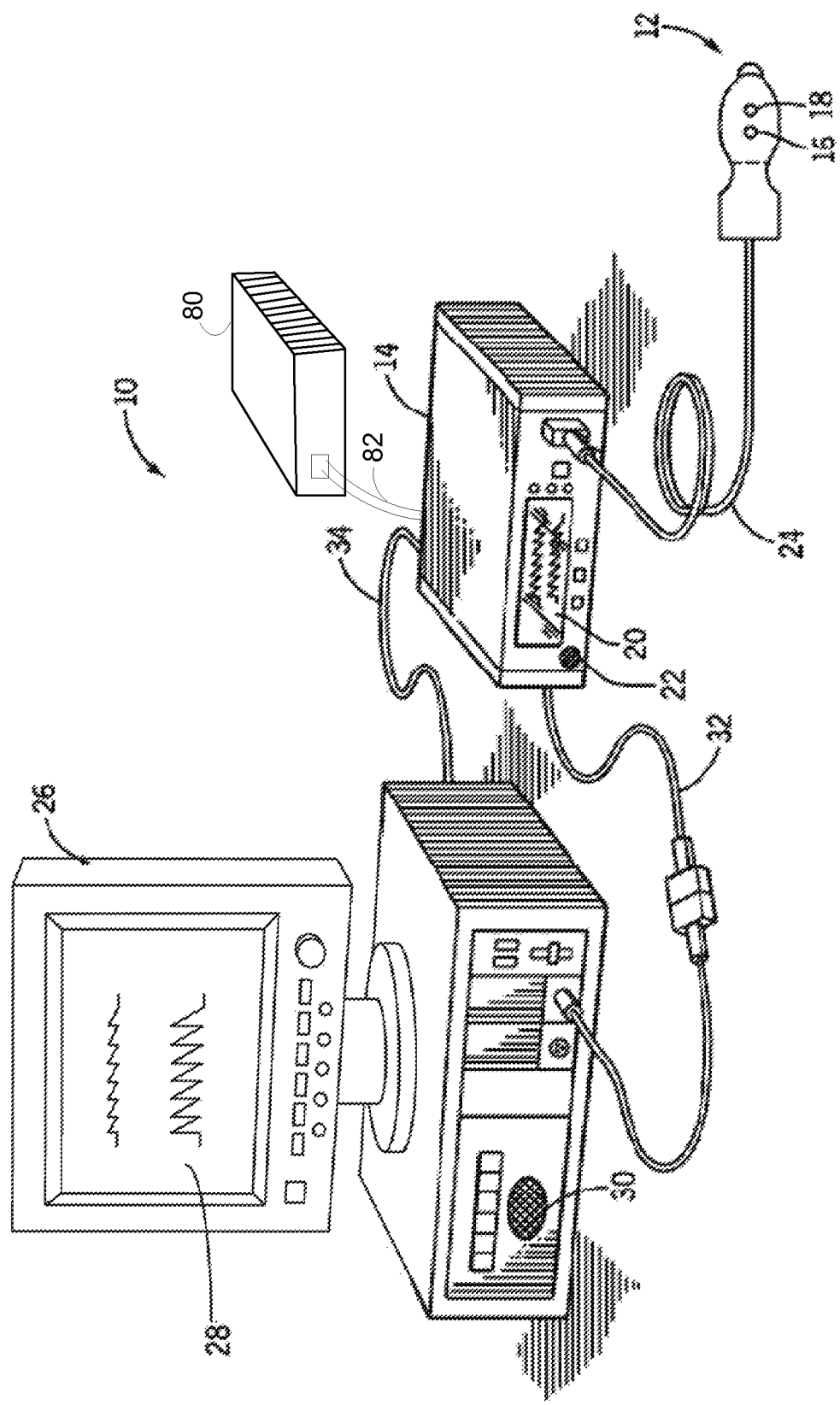
FIG. 1 shows an illustrative CNIBP monitoring system in accordance with an embodiment.

Continuous non-invasive blood pressure ("CNIBP") monitoring systems may be used to obtain physiological parameter values (e.g., blood pressure, blood oxygen saturation (referred to as an "SpO$_2$" measurement) and pulse rate values) from a subject during a sleep study. Changes in the blood pressure values obtained may be determined and analyzed in order to identify sleep events such as transitions between sleep stages, arousals, and apneaic events (e.g., hypopneic events). A subject's blood pressure may be monitored continuously using a PPG signal. A PPG signal may be detected using a pulse oximeter (or other similar device) and associated hardware, software, or both. A light sensor may be placed at a site on a subject such as a fingertip, toe, forehead or earlobe, or in the case of a neonate, across a foot. A light source may pass light through blood perfused tissue and photoelectrically sense the absorption of light in the tissue. For example, the CNIBP monitoring system may measure the intensity of light that is received at the light sensor as a function of time. A signal representing light intensity versus time or a mathematical manipulation of this signal (e.g., a scaled version thereof, a log taken thereof, a scaled version of a log taken thereof, etc.) may be referred to as the photoplethysmograph (PPG) signal. In addition, the term "PPG signal," as used herein, may also refer to an absorption signal (i.e., representing the amount of light absorbed by the tissue) or any suitable mathematical manipulation thereof. A processor may continuously analyze the PPG signal in order to continuously monitor a subject's blood pressure.

CNIBP monitoring systems may need to be recalibrated over time to accurately detect blood pressure. For example, physiological changes in a subject may cause a CNIBP monitoring system to become inaccurate. Recalibration may be performed by measuring a patient's blood pressure (or a reference blood pressure) and corresponding updated or refined values for one or more constants or parameters used in the blood pressure measurement determination. These updated or refined constant or parameter values may then be used to determine the patient's blood pressure until the next recalibration sequence is performed (or for some predetermined length of time).

Recalibration may be performed: 1) initially after device or monitoring initialization; 2) prior to a subject falling asleep; 3) after signaled recalibration events; 4) periodically on a predetermined or other suitable event-driven schedule; or 5) at any combination of the aforementioned times. An exemplary event that may cause recalibration to be performed is when detected blood pressure values are outside a pre-defined threshold of the moving average. In some embodiments, recalibration may be stopped after the subject falls asleep. For example, the subject's blood pressure may be used to determine when the subject is asleep in order to determine when recalibration may be stopped. This may be useful in sleep studies where recalibration can potentially disturb a subject's sleep state.

FIG. 1 is a perspective view of an embodiment of a CNIBP monitoring system 10 that may be used to calculate blood pressure values in order to detect sleep events. System 10 may include a sensor 12 and a monitor 14. Sensor 12 may include an emitter 16 for emitting light at one or more wavelengths into a subject's tissue. A detector 18 may also be provided in sensor 12 for detecting the light originally from emitter 16 that emanates from the subject's tissue after passing through the tissue.

According to another embodiment and as will be described, system 10 may include a plurality of sensors forming a sensor array in lieu of single sensor 12. Each of the sensors of the sensor array may be a complementary metal oxide semiconductor (CMOS) sensor. Alternatively, each sensor of the array may be a charged coupled device (CCD) sensor. In another embodiment, the sensor array may be made up of a combination of CMOS and CCD sensors. The CCD sensor may comprise a photoactive region and a transmission region for receiving and transmitting data whereas the CMOS sensor may be made up of an integrated circuit having an array of pixel sensors. Each pixel may have a photodetector and an active amplifier.

According to an embodiment emitter 16 and detector 18 may be on opposite sides of a digit such as a finger or toe, in which case the light that is emanating from the tissue has passed completely through the digit. In an embodiment, detector 18 (e.g., a reflective sensor) may be positioned anywhere a strong pulsatile flow may be detected (e.g., over arteries in the neck, wrist, thigh, ankle, ear, or any other suitable location). In an embodiment, emitter 16 and detector 18 may be arranged so that light from emitter 16 penetrates the tissue and is reflected by the tissue into detector 18, such as a sensor designed to obtain pulse oximetry or CNIBP data from a patient's forehead.

In an embodiment, the sensor or sensor array may be connected to, and draw its power from monitor 14 as shown. In another embodiment, the sensor may be wirelessly connected to monitor 14 and include its own battery or similar power supply (not shown). Monitor 14 may be configured to calculate physiological parameters (e.g., blood pressure) based at least in part on data received from sensor 12 relating to light emission and detection. In an alternative embodiment, the calculations may be performed on the monitoring device itself and the result of the light intensity reading may be passed to monitor 14. Further, monitor 14 may include a display 20 configured to display the physiological parameters or other information about the system. In the embodiment shown, monitor 14 may also include a speaker 22 to provide an audible sound that may be used in various other embodiments, such as for example, sounding an audible alarm in the event that a subject's physiological parameters are not within a predefined normal range.

In an embodiment, sensor 12, or the sensor array, may be communicatively coupled to monitor 14 via a cable 24. However, in other embodiments, a wireless transmission device (not shown) or the like may be used instead of or in addition to cable 24.

In the illustrated embodiment system 10 may also include a multi-parameter subject monitor 26. The monitor may be cathode ray tube type, a flat panel display (as shown) such as a liquid crystal display (LCD) or a plasma display, or any other type of monitor now known or later developed. Multi-parameter subject monitor 26 may be configured to calculate physiological parameters and to provide a display 28 for information from monitor 14 and from other medical monitoring devices or systems (not shown). For example, multi-parameter subject monitor 26 may be configured to display an estimate of a subject's blood pressure from monitor 14, $SpO_2$ measurement generated by monitor 14, and pulse rate information from monitor 14.

Monitor 14 may be communicatively coupled to multi-parameter subject monitor 26 via a cable 32 or 34 that is coupled to a sensor input port or a digital communications port, respectively and/or may communicate wirelessly (not shown). In addition, monitor 14 and/or multi-parameter subject monitor 26 may be coupled to a network to enable the sharing of information with servers or other workstations (not shown). Monitor 14 may be powered by a battery (not shown) or by a conventional power source such as a wall outlet.

Calibration device 80, which may be powered by monitor 14, a battery, or by a conventional power source such as a wall outlet, may include any suitable blood pressure calibration device. For example, calibration device 80 may take the form of any invasive or non-invasive blood pressure monitoring or measuring system used to generate reference blood pressure measurements for use in calibrating the CNIBP monitoring techniques described herein. Such calibration devices may include, for example, an aneroid or mercury sphygmomanometer and occluding cuff, a pressure sensor inserted directly into a suitable artery of a subject, or any other device or mechanism used to sense, measure, determine, or derive a reference blood pressure measurement. In some embodiments, calibration device 80 may include a manual input device (not shown) used by an operator to manually input reference blood pressure measurements obtained from some other source (e.g., an external invasive or non-invasive blood pressure measurement system).

Calibration device 80 may also access reference blood pressure measurements stored in memory (e.g., RAM, ROM, or a storage device). For example, in some embodiments, calibration device 80 may access reference blood pressure measurements from a relational database stored within calibration device 80, monitor 14, or multi-parameter subject monitor 26. As described in more detail below, the reference blood pressure measurements generated or accessed by calibration device 80 may be updated in real-time, resulting in a continuous source of reference blood pressure measurements for use in continuous or periodic calibration. Alternatively, reference blood pressure measurements generated or accessed by calibration device 80 may be updated periodically, and calibration may be performed on the same periodic cycle. In the depicted embodiments, calibration device 80 is connected to monitor 14 via cable 82. In embodiments, calibration device 80 may be a stand-alone device that may be in wireless communication with monitor 14. Reference blood pressure measurements may then be wirelessly transmitted to monitor 14 for use in calibration. In embodiments, calibration device 80 may be completely integrated within monitor 14.

Figure 2:
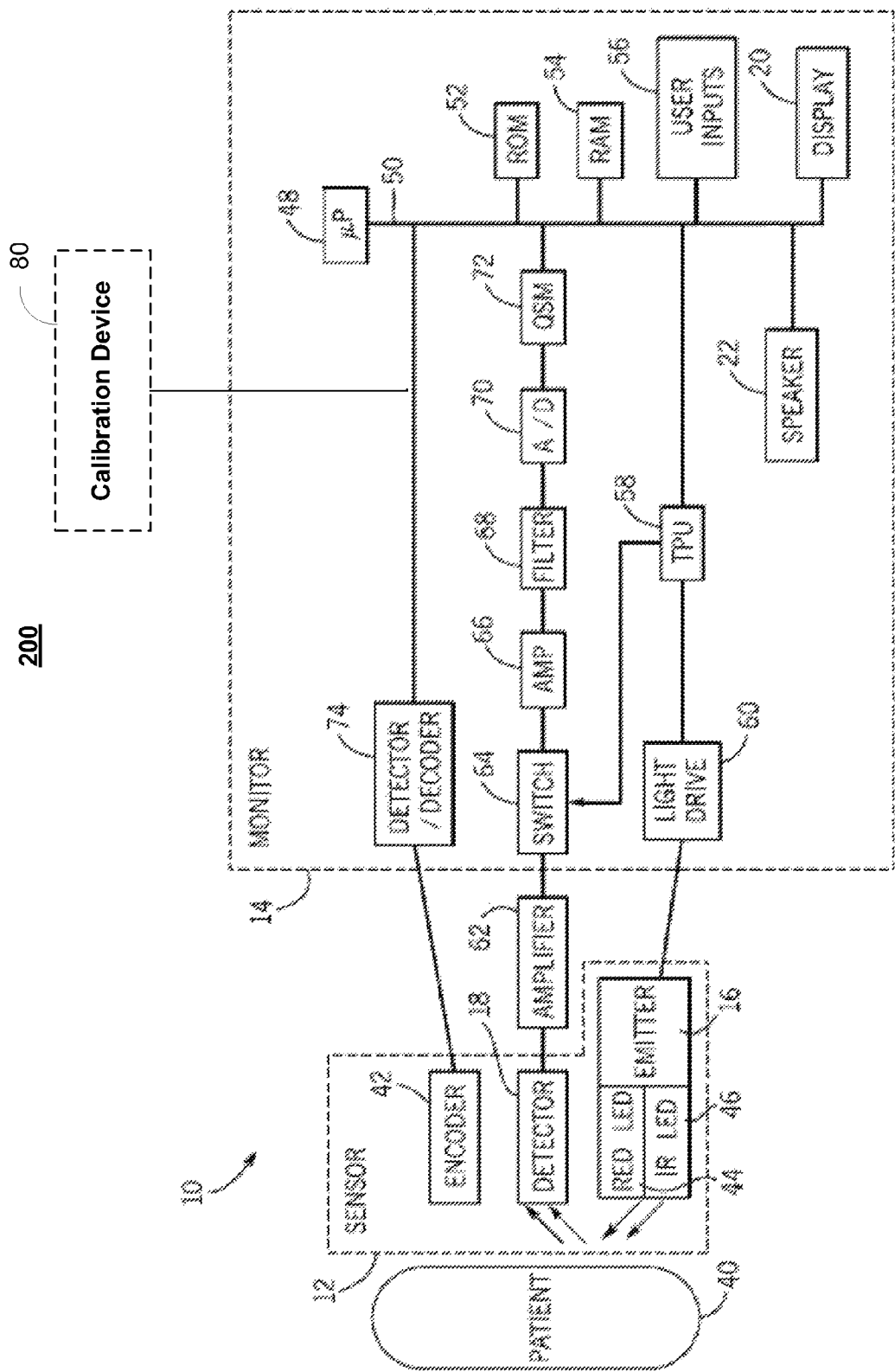
FIG. 2 is a block diagram of the illustrative CNIBP monitoring system of FIG. 1 coupled to a subject in accordance with an embodiment.

FIG. 2 is a block diagram of a CNIBP monitoring system, such as system 10 of FIG. 1, which may be coupled to a subject 40 in accordance with an embodiment. Certain illustrative components of sensor 12 and monitor 14 are illustrated in FIG. 2. Sensor 12 may include emitter 16, detector 18, and encoder 42. In an embodiment, emitter 16 may be configured to emit at least one wavelength of light (e.g., RED or IR) into a subject's tissue 40. For calculating $SpO_2$, emitter 16 may include a RED light emitting light source such as RED light emitting diode (LED) 44 and an IR light emitting light source such as IR LED 46 for emitting light into the subject's tissue 40. In other embodiments, emitter 16 may include a light emitting light source of a wavelength other than RED or IR. In one embodiment the RED wavelength may be between about 600 nm and about 700 nm, and the IR wavelength may be between about 800 nm and about 1000 nm. In embodiments where a sensor array is used in place of single sensor, each sensor may be configured to emit a single wavelength. For example, a first sensor emits only a RED light while a second only emits an IR light.

As used herein, the term "light" may refer to energy produced by radiative sources and may include one or more of ultrasound, radio, microwave, millimeter wave, infrared, visible, ultraviolet, gamma ray or X-ray electromagnetic radiation. As used herein, light may also include any wavelength within the radio, microwave, infrared, visible, ultraviolet, or X-ray spectra, and that any suitable wavelength of electromagnetic radiation may be appropriate for use with the present techniques. Detector 18 may be chosen to be specifically sensitive to the chosen targeted energy spectrum of the emitter 16.

In an embodiment, detector 18 may be configured to detect the intensity of light at the emitted wavelengths (or any other suitable wavelength). Alternatively, each sensor in the array may be configured to detect an intensity of a single wavelength. In operation, light may enter detector 18 after passing through the subject's tissue 40. Detector 18 may convert the intensity of the received light into an electrical signal. The light intensity is directly related to the absorbance and/or reflectance of light in the tissue 40. That is, when more light at a certain wavelength is absorbed or reflected, less light of that wavelength is received from the tissue by the detector 18. After converting the received light to an electrical signal, detector 18 may send the signal to monitor 14, where physiological parameters may be calculated based on the absorption of one or more of the RED and IR (or other suitable) wavelengths in the subject's tissue 40.

In an embodiment, encoder 42 may contain information about sensor 12, such as what type of sensor it is (e.g., whether the sensor is intended for placement on a forehead or digit) and the wavelength or wavelengths of light emitted by emitter 16. This information may be used by monitor 14 to select appropriate algorithms, lookup tables and/or calibration coefficients stored in monitor 14 for calculating the subject's physiological parameters.

Encoder 42 may contain information specific to subject 40, such as, for example, the subject's age, weight and diagnosis. This information may allow monitor 14 to determine, for example, subject-specific threshold ranges in which the subjects physiological parameter measurements should fall and to enable or disable additional physiological parameter algorithms. Encoder 42 may, for instance, be a coded resistor which stores values corresponding to the type of sensor 12 or the type of each sensor in the sensor array, the wavelength or wavelengths of light emitted by emitter 16 on each sensor of the sensor array, and/or the subject's characteristics. In an embodiment, encoder 42 may include a memory on which one or more of the following information may be stored for communication to monitor 14: the type of the sensor 12; the wavelength or wavelengths of light emitted by emitter 16; the particular wavelength each sensor in the sensor array is monitoring; a signal threshold for each sensor in the sensor array; any other suitable information; or any combination thereof.

In an embodiment, signals from detector 18 and encoder 42 may be transmitted to monitor 14. In the embodiment shown, monitor 14 may include a general-purpose microprocessor 48 connected to an internal bus 50. Microprocessor 48 may be adapted to execute software, which may include an operating system and one or more applications, as part of performing the functions described herein. Also connected to bus 50 may be a read-only memory (ROM) 52, a random access memory (RAM) 54, user inputs 56, display 20, and speaker 22.

RAM 54 and ROM 52 are illustrated by way of example, and not limitation. Any suitable computer-readable media may be used in the system for data storage. Computer-readable media are capable of storing information that can be interpreted by microprocessor 48. This information may be data or may take the form of computer-executable instructions, such as software applications, that cause the microprocessor to perform certain functions and/or computer-implemented methods. Depending on the embodiment, such computer-readable media may include computer storage media and communication media. Computer storage media may include volatile and non-volatile, removable and non-removable media implemented in any method or technology for storage of information such as computer-readable instructions, data structures, program modules or other data. Computer storage media may include, but is not limited to, RAM, ROM, EPROM, EEPROM, flash memory or other solid state memory technology, CD-ROM, DVD, or other optical storage, magnetic cassettes, magnetic tape, magnetic disk storage or other magnetic storage devices, or any other medium which can be used to store the desired information and which can be accessed by components of the system.

In the embodiment shown, a time processing unit (TPU) 58 may provide timing control signals to a light drive circuitry 60, which may control when emitter 16 is illuminated and multiplexed timing for the RED LED 44 and the IR LED 46. TPU 58 may also control the gating-in of signals from detector 18 through an amplifier 62 and a switching circuit 64. These signals are sampled at the proper time, depending upon which light source is illuminated. The received signal from detector 18 may be passed through an amplifier 66, a low pass filter 68, and an analog-to-digital converter 70. The digital data may then be stored in a queued serial module (QSM) 72 (or buffer) for later downloading to RAM 54 as QSM 72 fills up. In one embodiment, there may be multiple separate parallel paths having amplifier 66, filter 68, and A/D converter 70 for multiple light wavelengths or spectra received.

In an embodiment, microprocessor 48 may determine the subject's physiological parameters, such as blood pressure, $SpO_2$, and pulse rate, using various algorithms and/or look-up tables based on the value of the received signals and/or data corresponding to the light received by detector 18. Signals corresponding to information about subject 40, and particularly about the intensity of light emanating from a subject's tissue over time, may be transmitted from encoder 42 to a decoder 74. These signals may include, for example, encoded information relating to subject characteristics. Decoder 74 may translate these signals to enable the microprocessor to determine the thresholds based on algorithms or lookup tables stored in ROM 52. User inputs 56 may be used to enter information about the subject, such as age, weight, height, diagnosis, medications, treatments, and so forth. In an embodiment, display 20 may exhibit a list of values which may generally apply to the subject, such as, for example, age ranges or medication families, which the user may select using user inputs 56.

The optical signal through the tissue can be degraded by noise, among other sources. One source of noise is ambient light that reaches the light detector. Another source of noise is electromagnetic coupling from other electronic instruments. Movement of the subject also introduces noise and affects the signal. For example, the contact between the detector and the skin, or the emitter and the skin, can be temporarily disrupted when movement causes either to move away from the skin. In addition, because blood is a fluid, it responds differently than the surrounding tissue to inertial effects, thus resulting in momentary changes in volume at the point to which the sensor or probe is attached.

Noise (e.g., from patient movement) can degrade a CNIBP or pulse oximetry signal relied upon by a physician, without the physician's awareness. This is especially true if the monitoring of the subject is remote, the motion is too small to be observed, or the doctor is watching the instrument or other parts of the subject and not the sensor site. Processing CNIBP or pulse oximetry (i.e., PPG) signals may involve operations that reduce the amount of noise present in the signals or otherwise identify noise components in order to prevent them from affecting measurements of physiological parameters derived from the PPG signals.

CNIBP monitoring system 10 may also include calibration device 80. Although shown external to monitor 14 in the example of FIG. 2, calibration device 80 may additionally or alternatively be internal to monitor 14. Calibration device 80 may be connected to internal bus 50 of monitor 14. As described in more detail below, reference blood pressure measurements from calibration device 80 may be accessed by microprocessor 48 for use in calibrating the CNIBP measurements.

Figure 3:
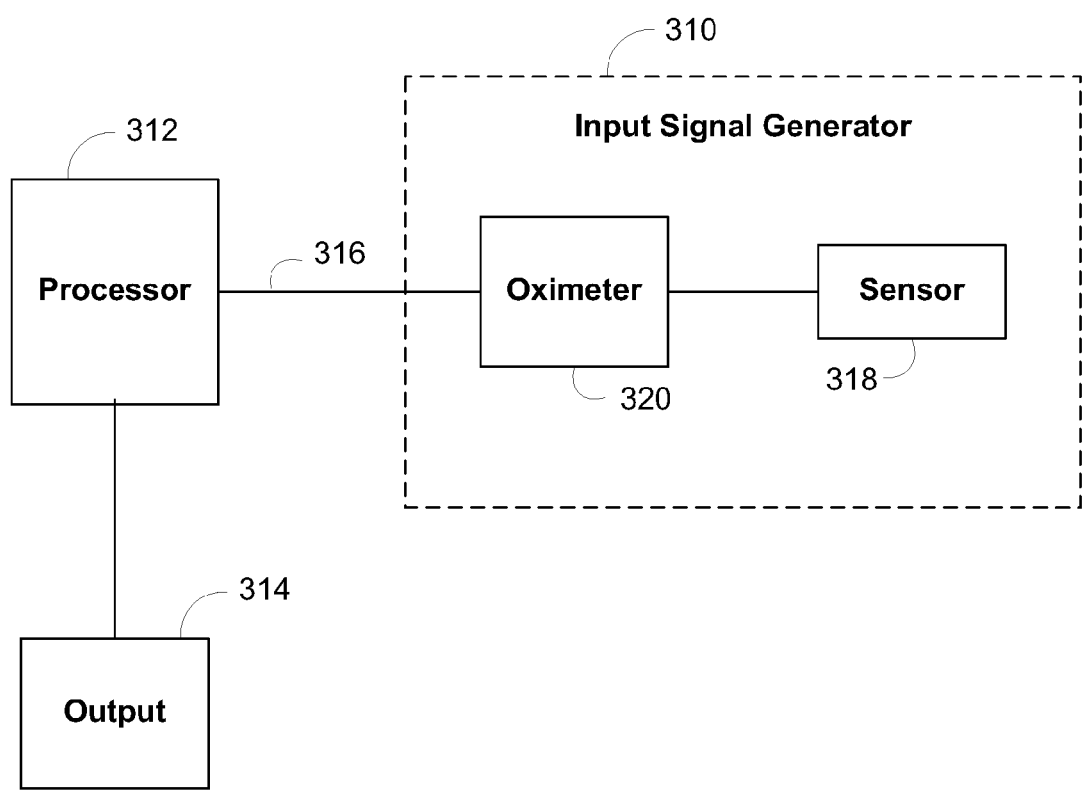
FIG. 3 is a block diagram of an illustrative signal processing system in accordance with some embodiments.

FIG. 3 is an illustrative processing system 300 in accordance with an embodiment. In this embodiment, input signal generator 310 generates an input signal 316. As illustrated, input signal generator 310 may include oximeter 320 (or similar device) coupled to sensor 318, which may provide as input signal 316, a PPG signal. It will be understood that input signal generator 310 may include any suitable signal source, signal generating data, signal generating equipment, or any combination thereof to produce signal 316.

In this embodiment, signal 316 may be coupled to processor 312. Processor 312 may be any suitable software, firmware, and/or hardware, and/or combinations thereof for processing signal 316. For example, processor 312 may include one or more hardware processors (e.g., integrated circuits), one or more software modules, computer-readable media such as memory, firmware, or any combination thereof. Processor 312 may, for example, be a computer or may be one or more chips (i.e., integrated circuits). Processor 312 may perform some or all of the calculations associated with the blood pressure monitoring methods of the present disclosure. For example, processor 312 may determine the time difference between a first time and a second time associated with a first pulse and a second pulse of two PPG signals obtained from input signal generator 310. Processor 312 may also be configured to determine and analyze changes in blood pressure in order to identify a steep event. The techniques for determining and analyzing changes in blood pressure in the present disclosure are further discussed below. Processor 312 may also perform any suitable signal processing of signal 316 to filter signal 316, such as any suitable band-pass filtering, adaptive filtering, closed-loop filtering, and/or any other suitable filtering, and/or any combination thereof.

Processor 312 may be coupled to one or more memory devices (not shown) or incorporate one or more memory devices such as any suitable volatile memory device (e.g., RAM, registers, etc.), non-volatile memory device (e.g., ROM, EPROM, magnetic storage device, optical storage device, flash memory, etc.), or both. Processor 312 may be coupled to a calibration device (not shown) that may generate or receive as input reference blood pressure measurements for use in calibrating CNIBP calculations.

Processor 312 may be coupled to output 314. Output 314 may be any suitable output device such as, for example, one or more medical devices (e.g., a medical monitor that displays various physiological parameters, a medical alarm, or any other suitable medical device that either displays physiological parameters or uses the output of processor 212 as an input), one or more display devices (e.g., monitor, PDA, mobile phone, any other suitable display device, or any combination thereof), one or more audio devices, one or more memory devices (e.g., hard disk drive, flash memory, RAM, optical disk, any other suitable memory device, or any combination thereof), one or more printing devices, any other suitable output device, or any combination thereof.

System 300 may be incorporated into system 10 (FIGS. 1 and 2) in which, for example, input signal generator 310 may be implemented as parts of sensor 12 and monitor 14 and processor 312 may be implemented as part of monitor 14. In some embodiments, portions of system 300 may be configured to be portable. For example, all or a part of system 300 may be embedded in a small, compact object carried with or attached to the subject (e.g., a watch or cellular telephone). In such embodiments, a wireless transceiver (not shown) may also be included in system 300 to enable wireless communication with other components of system 10. As such, system 10 may be part of a fully portable and continuous blood pressure monitoring solution.

According to the present disclosure, blood pressure measurements may be derived by detecting at least one PPG signal obtained from a sensor or probe, and calculating blood pressure based at least in part on the at least one PPG signal. In some embodiments, a sensor or probe may detect a first PPG signal at a first location on a subject and a second PPG signal at a second location on the subject. CNIBP monitoring system 10 or system 300 may also detect a first time associated with the first PPG signal and a corresponding time associated with the second PPG signal. The time difference between the corresponding times may be determined and used to compute a blood pressure measurement. The measurements may be computed on a continuous or periodic basis. Computing the blood pressure may comprise performing the calculation:

$$P = a + b \cdot \ln(T)$$

Where P is the estimated blood pressure, T is the time difference, and a and b are constants associated with the physiological state of the subject. Chen et al. U.S. Pat. No. 6,599,251, which is hereby incorporated by reference herein in its entirety, discloses techniques for CNIBP monitoring using time differences between pulses detected at two locations on a subject that may be used in conjunction with the present disclosure.

In some embodiments, a sensor or probe may detect a PPG signal from a location on a subject, and at least two characteristic points in the detected PPG signal may be identified. Characteristic points in the PPG signal may be identified in a number of ways. In some embodiments, the turning points of 1st, 2nd, 3rd (or any other) derivative of the PPG signal are used as characteristic points. Additionally or alternatively, points of inflection in the PPG signal (or any suitable derivative thereof) may also be used as characteristic points of the PPG signal. The time difference between the characteristic points in the detected PPG signal may then be used to determine the blood pressure of the subject. Sethi et al. U.S. patent application Ser. No. 12/242,238, filed Sep. 30, 2008, entitled "Systems And Methods For Non-Invasive Blood Pressure Monitoring," which is hereby incorporated by reference herein in its entirety, discloses techniques for CNIBP monitoring using the time difference between characteristic points in the PPG signal, that may be used in conjunction with the present disclosure.

In some embodiments, a sensor or probe may detect a PPG signal from a location on a subject, and locations of pulses within the PPG signal may be identified. An area within a particular pulse may be measured. For example, the area, may be of just the upstroke, downstroke or the entire pulse. The area may be measured relative to a time-domain axis or a baseline of the pulse. The pulse may also be split into multiple sections, and the area of each section may be measured. The area of one portion of the pulse may correspond to systolic blood pressure while the area of another portion may correspond to diastolic blood pressure. Empirical data may then be used to determine the blood pressure of a subject from the measured area. Sethi et al. U.S. patent application Ser. No. 12/242,867, filed Sep. 30, 2008, now U.S. Pat. No. 8,398,556, entitled "Systems And Methods For Non-Invasive Continuous Blood Pressure Determination," which is hereby incorporated by reference herein in its entirety, discloses techniques for CNIBP monitoring by measuring the area within a particular pulse in a PPO signal, that may be used in conjunction with the present disclosure.

Figure 4:
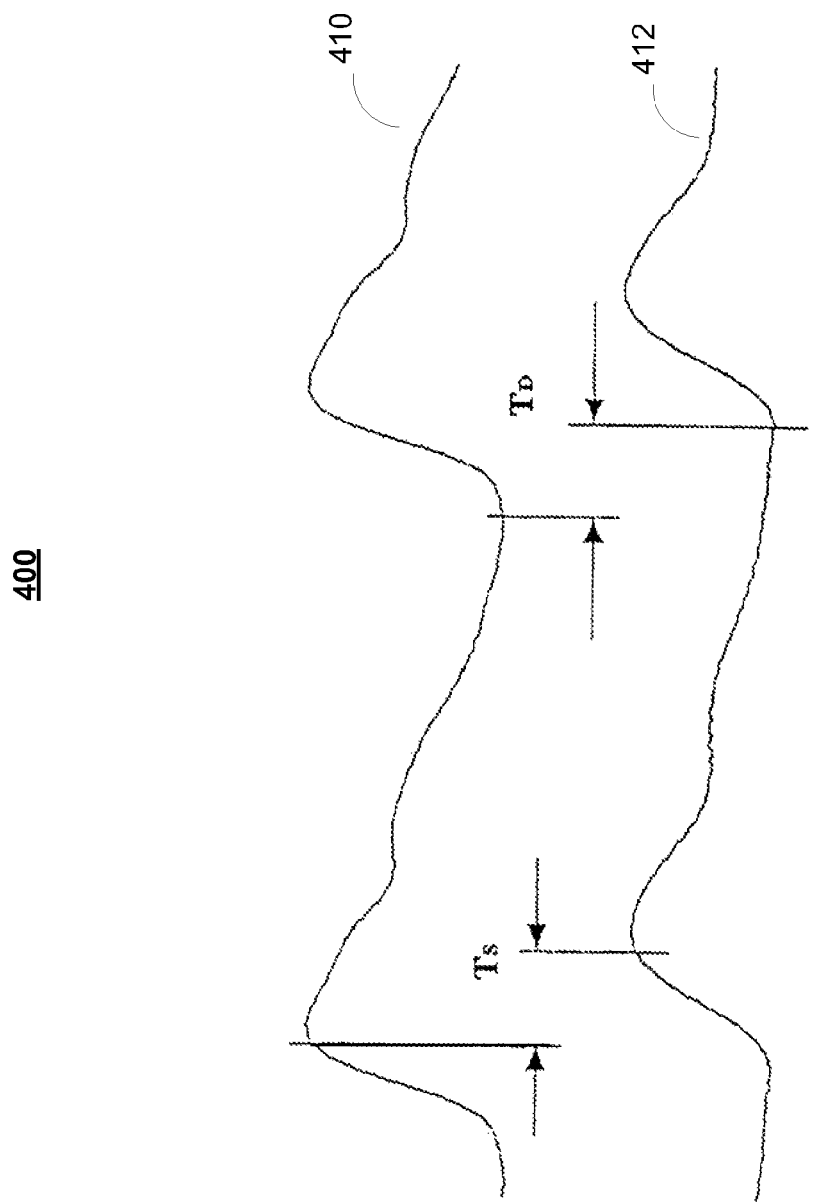
FIG. 4 shows two PPG signals that may be detected by the CNIBP monitoring system of FIG. 1 or FIG. 3.

The present disclosure may be applied to measuring systolic blood pressure, diastolic blood pressure, or both systolic and diastolic blood pressure on an on-going, continuous, or periodic basis. For example, FIG. 4 shows a first PPG signal 410 and a second PPG signal 412, which may be detected by a sensor or probe at two locations on a subject. $T_S$ and $T_D$ are time differences that may be measured between first PPG signal 410 and second PPG signal 412 and used to calculate systolic and diastolic blood pressure values respectively.

Figure 5:
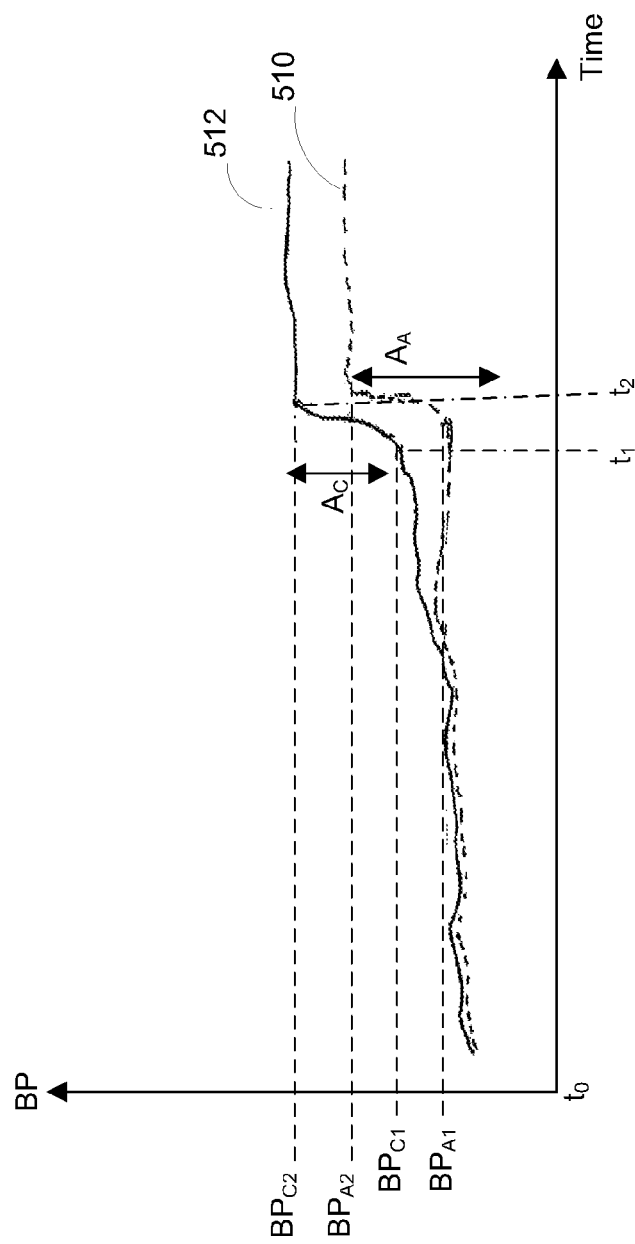
FIG. 5 shows an illustrative plot tracking blood pressure against time in accordance with some embodiments.

After calculating the blood pressure of a subject using any of the techniques discussed above or any other suitable technique, changes in the blood pressure may be determined and analyzed in order to identify a sleep event. FIG. 5 shows an illustrative actual blood pressure plot 510 and CNIBP blood pressure monitoring plot 512 that each track blood pressure against time in accordance with some embodiments. Actual blood pressure plot 510 may show the actual blood pressure values of the subject over a period of time while CNIBP blood pressure monitoring plot 512 may show the blood pressure values measured by, for example, CNIBP monitoring system 10 (FIGS. 1 and 2) or processing system 300 (FIG. 3) over a period of time.

CNIBP blood pressure monitoring plot 512 of FIG. 5 may be generated without recalibration of a CNIBP monitoring system such as system 10 (FIGS. 1 and 2) or processing system 300 (FIG. 3). In an embodiment the CNIBP monitoring system may be recalibrated until the subject falls asleep. As shown, plot 512 drifts away from actual blood pressure plot 510 as time increases. Thus, plot 512 may not be useful detecting an accurate reading of a subject's blood pressure. However, plot 512 may be useful in a sleep study. For example, localized blood pressure changes may still be determined accurately from CNIBP blood pressure monitoring plot 512. As shown, the actual blood pressure values of plot 510 at times $t_1$ and $t_2$ may be $BP_{A1}$ and $BP_{A2}$ respectively while the CNIBP determined blood pressure values of plot 512 may be $BP_{C1}$ and $BP_{C2}$ at times $t_1$ and $t_2$ respectively. The actual localized blood pressure change between times $t_1$ and $t_2$ ($A_A$) and the blood pressure change measured by a CNIBP monitoring system between times $t_1$ and $t_2$ ($A_C$) may be substantially equal in value. Localized blood pressure changes may be used to identify sleep events.

Figure 6:
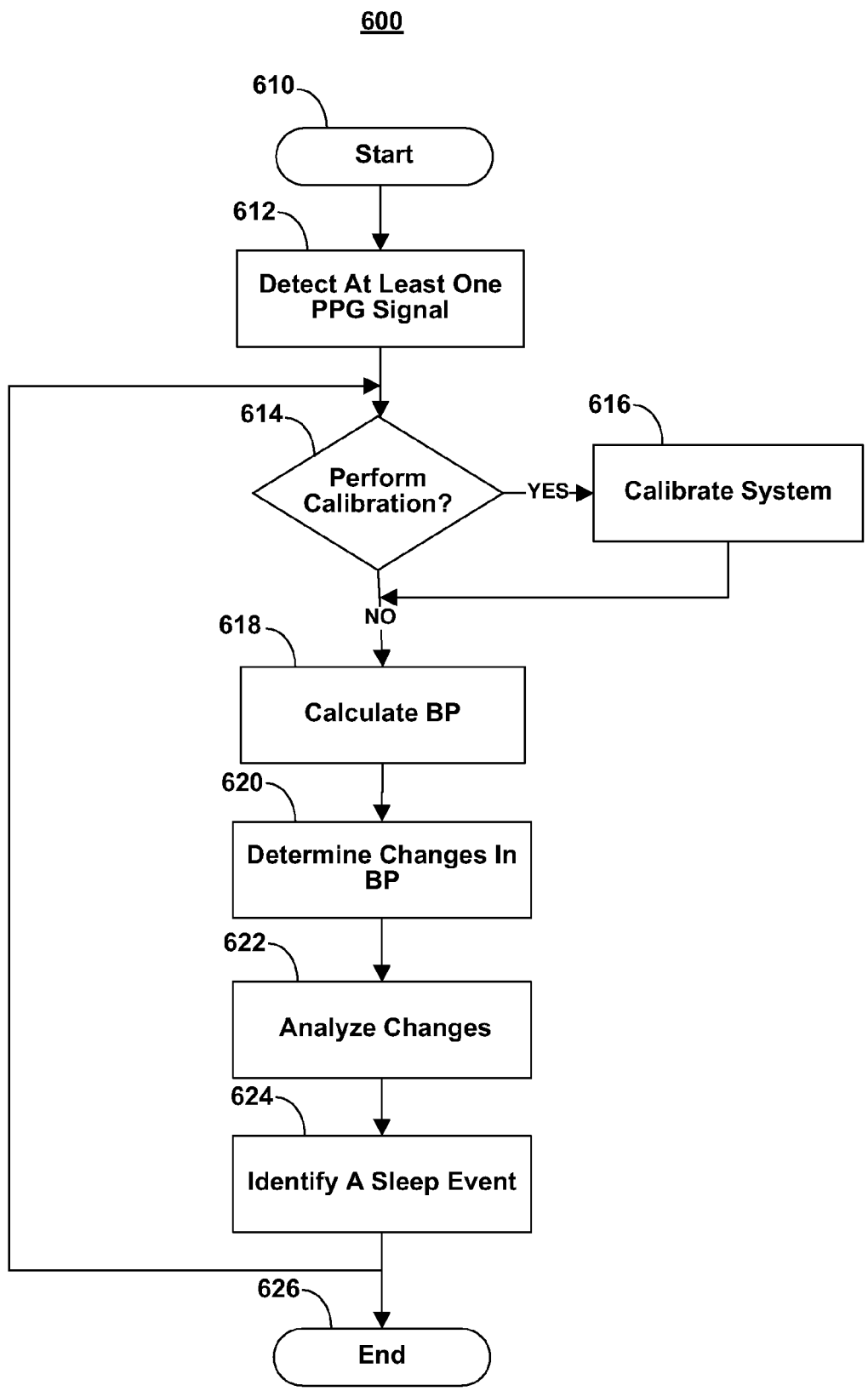
FIGS. 6 and 7 show illustrative processes for detecting sleep events in accordance with some embodiments.

FIG. 6 shows illustrative process 600 for detecting a sleep event during, for example, a sleep study. Process 600 begins at step 610. At step 612, the system detects at least one PPG signal. For example, monitor 14 (FIGS. 1 and 2) may be used to detect at least one PPG signal from subject 40 (FIG. 2) using, for example, sensor 12 (FIGS. 1 and 2). At step 614, it is determined whether the system is to be calibrated. In some embodiments, process 600 may proceed automatically with the sleep study without calibrating the system. In other embodiments, the system may be calibrated before, but not during, the sleep study. If a calibration needs to be performed, (e.g., the system has been set up to automatically recalibrate before a sleep study), the system is recalibrated at step 616. As discussed above, recalibration may be performed by measuring a patients blood pressure (or a reference blood pressure) and updating or refining values for one or more constants or parameters used in the blood pressure measurement determination. These updated or refined constant or parameter values may then be used to determine the patient's blood pressure until the next calibration sequence is performed (or for some predetermined length of time).

If calibration does not need to be performed at step 614 or after the system is recalibrated at step 616, the system proceeds to step 618, where blood pressure is calculated by the system.

As discussed above, in some embodiments, a first PPG signal and a second PPG signal may be detected from two locations on a subject. A time difference between a first time and a second time associated respectively with pulses in the first and second signals may be measured and used to compute blood pressure values. In some embodiments, a PPG signal may be detected from a location on a subject and at least two characteristic points in the PPG signal may be detected. A time difference between two of the at least two characteristic points may be measured and used to calculate blood pressure values. In some embodiments, a PPG signal may be detected from a location on a subject and locations of pulses in the PPG signal may be received. An area under a portion of one of the pulses may be measured and used to calculate blood pressure values.

After calculating the blood pressure at step 618, changes in the blood pressure are determined at step 620 and analyzed at step 622 in order to identify a sleep event at step 624. The blood pressure of a subject is more variable during REM sleep stages than during non-REM sleep stages. Accordingly, in an embodiment, the variation of a subject's blood pressure can be determined and used to identify transitions between different sleep stages. Additionally, the blood pressure of a subject is typically lower when the subject is asleep than when the subject is awake. As such, a sleep arousal typically results in an increase in blood pressure, which may be detected in order to identify a sleep arousal. After a sleep arousal, a subject may fall asleep again. This may result in a decrease in blood pressure, which may be detected to identify the end of a sleep arousal. Furthermore, a steep apneaic event is often accompanied by a decrease in oxygen saturation, which results in a drastic decrease or abrupt changes in blood pressure. For example, central apnea is characterized by a pronounced decrease in blood pressure while obstructive apnea is characterized by abrupt blood pressure changes. In an embodiment, a steep apneaic event may be identified by detecting such decreases or abrupt changes in blood pressure. A sleep apneaic event may be followed by a sleep arousal, resulting in an increase in blood pressure. In an embodiment, such an increase may be detected in order to identify the end of an apneaic event. Techniques for identifying a sleep event by determining and analyzing changes in blood pressure will be discussed below in connection with FIG. 7. After step 624, process 600 returns to calibration decision 614 to repeat the remaining steps until the process ends at step 626.

Figure 7:
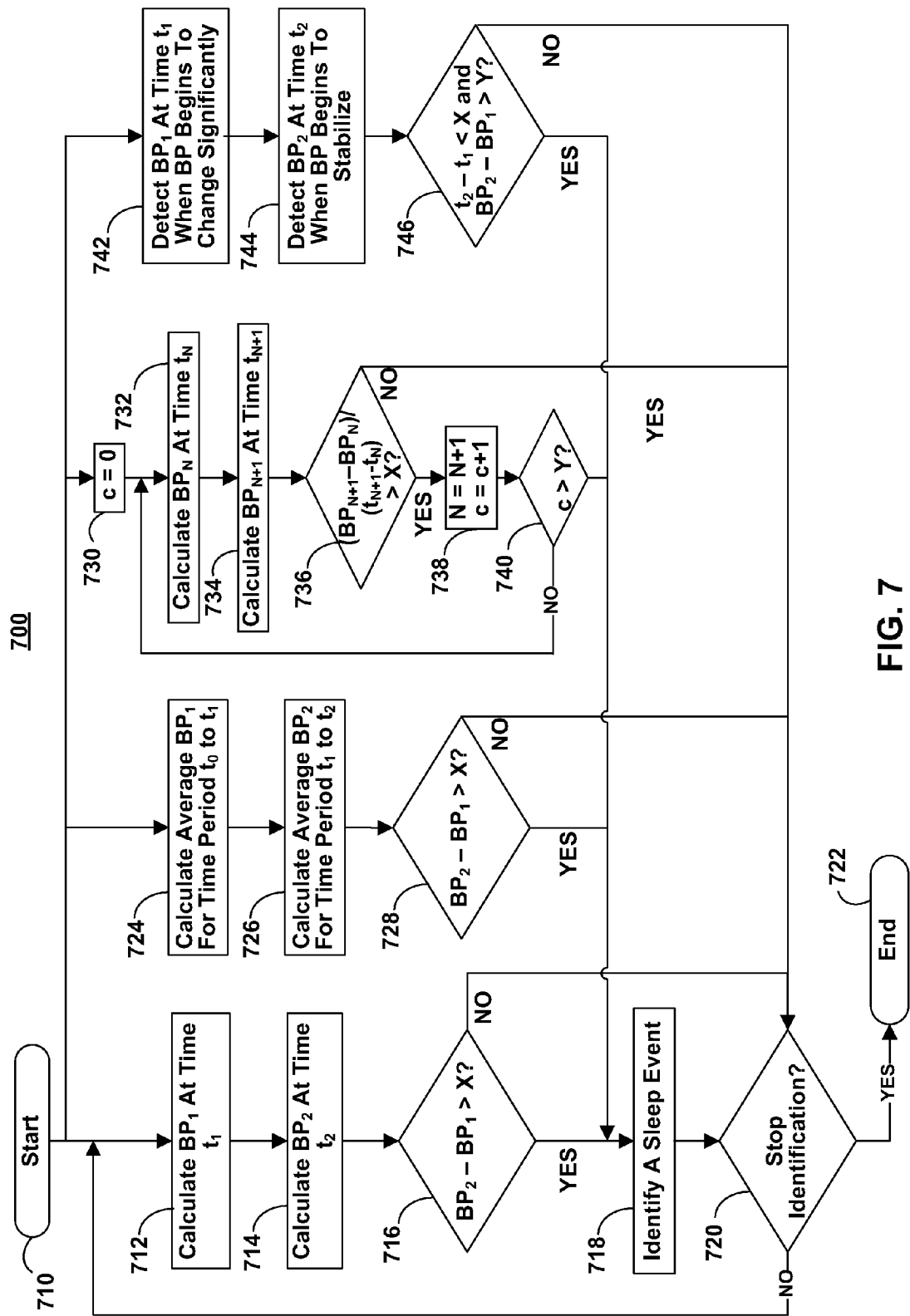

FIG. 7 shows illustrative process 700 for identifying a sleep event in a subject by determining and analyzing changes in blood pressure. Process 700 includes four sub-processes that may be performed in parallel. In order to identify a sleep event, one or more of the four sub-processes may be performed at the same time. Process 700 will be described with continued references to blood pressure plots 510 and 512 (FIG. 5). Process 700 begins at step 710.

In an embodiment the process of identifying a sleep event may begin at steps 712, 724, 730, and 742, which may be run substantially in parallel. At step 712, a first blood pressure value that is associated with a first time is calculated for the subject. For example, blood pressure value $BP_{C1}$ (FIG. 5) that is associated with time $t_1$ (FIG. 5) may be calculated by CNIBP monitoring system 10 (FIGS. 1 and 2) or processing system 300 (FIG. 3). At step 714, a second blood pressure value that is associated with a second time is calculated. For example, blood pressure value $BPC_2$ (FIG. 5) that is associated with time $t_2$ (FIG. 5) may be calculated by CNIBP monitoring system 10 (FIGS. 1 and 2) or processing system 300 (FIG. 3). At step 716, a blood pressure difference between the first blood pressure value and the second blood pressure value may be measured and compared to a pre-defined threshold value. For example, blood pressure difference $A_C$ (FIG. 5) may be measured and compared to a pre-defined threshold value. If the blood pressure difference $A_C$ is greater than the threshold, then a notification may be provided to step 718 for use in determining whether a sleep event should be identified. If it is determined at step 716 that the blood pressure difference is not greater than the pre-defined threshold value, process 700 may proceed to step 720.

In some embodiments of the present disclosure, pre-defined threshold values may be determined based at least in part on a subject's physiological state. For example, a pre-defined threshold value may be determined for the identification of arousal of a subject while another pre-defined threshold value may be determined for the identification of sleep apnea in the subject. When calculated parameters associated with the subject's blood pressure are greater than or less than a pre-defined threshold value, a sleep event may be identified.

Steps 724-728 may be performed substantially in parallel to steps 712-716 discussed above. At step 724, a long-term average blood pressure for the subject is calculated. For example, the average blood pressure for the time period between $t_0$ and $t_1$ or $t_2$ (FIG. 5) may be calculated by CNIBP monitoring system 10 (FIGS. 1 and 2) or processing system 300 (FIG. 3). At step 726, a short-term average blood pressure is calculated. For example, the average blood pressure for the time period between $t_1$ and $t_2$ (FIG. 5) may be calculated by CNIBP monitoring system 10 (FIGS. 1 and 2) or processing system 300 (FIG. 3). At step 728, a blood pressure difference between the long-term average blood pressure and the short-term average blood pressure may be measured and compared to a pre-defined threshold value. If the blood pressure difference is greater than the pre-defined threshold value, then a notification may be provided to step 718 for use in determining whether a sleep event should be identified. If it is determined that the blood pressure difference is not greater than the pre-defined threshold value, process 700 may proceed to step 720.

Steps 730-740 may be performed substantially in parallel to steps 712-716 and steps 724-728 discussed above. At step 730, a counter, c is set to zero. At step 732, a first blood pressure value that is associated with a first time, N is calculated for the subject. For example, blood pressure value $BP_{C1}$ (FIG. 5) that is associated with time $t_1$ (FIG. 5) may be calculated by CNIBP monitoring system to (FIGS. 1 and 2) or processing system 300 (FIG. 3). At step 734, a second blood pressure value that is associated with a second time, N+1 is calculated. At step 736, a ratio of the blood pressure difference between the first and second blood pressure values to the difference between the first and second times may be determined and compared to a first pre-defined threshold value. If the ratio is greater than the first pre-defined threshold value, process 700 may proceed to step 738. At step 738, the first time, N is set to the second time, N+1 and the counter is increased by one. Process 700 may then proceed to step 740 where the counter is compared to a second pre-defined threshold value. If the counter is greater than the second pre-defined threshold value, then a notification may be provided to step 718 for use in determining whether a sleep event should be identified. If the counter is less than the second pre-defined threshold value, then process 700 may return to step 732. Referring back to 736, if the ratio of the blood pressure difference between the first and second blood pressure values to the difference between the first and second times is not greater than the first pre-defined threshold value, process 700 may continue to step 720.

Steps 742-746 may be performed substantially in parallel to steps 712-716, steps 724-728, and steps 730-740 discussed above. At step 742, a first blood pressure value associated with a first time when the blood pressure of the subject begins to change significantly may be detected. For example, blood pressure value $BP_{C1}$ (FIG. 5) that is associated with time $t_1$ (FIG. 5) after which the blood pressure of the subject changes significantly from $BP_{C1}$ to $BP_{C2}$ may be detected by CNIBP monitoring system 10 (FIGS. 1 and 2) or processing system 300 (FIG. 3). At step 744, a second time when the blood pressure of the subject begins to stabilize may be detected. For example, blood pressure value $BP_{C2}$ (FIG. 5) that is associated with time $t_2$ (FIG. 5) after which the blood pressure of the subject remains substantially at blood pressure value $BP_{C2}$ may be detected by CNIBP monitoring system 10 (FIGS. 1 and 2) or processing system 300 (FIG. 3).

At step 746, a time difference between the first and second times is compared to a first pre-defined threshold value, and a blood pressure difference between the first and second blood pressure values is compared to a second pre-defined threshold value. If the time difference is less than the first pre-defined threshold value and the blood pressure difference is greater than the second pre-defined threshold value, then a notification may be provided to step 718 for use in determining whether a sleep event should be identified.

At step 718, the notifications received from steps 716, 728, 740, and 746 may be analyzed to determine whether a sleep event should be identified. In an embodiment, a sleep event may be indicated when a single notification is received. In another embodiment, a sleep event may be indicated when 2 or more notifications are received. After step 718, process 700 may proceed to step 720.

At step 720, it may be determined whether the process of sleep event identification is to continue. If process is to continue, process 700 may proceed to steps 712, 724, 730, and 742. Alternatively, process 700 may end at step 722.

After identifying one or more sleep events, the information acquired may be interpreted in isolation or in conjunction with other signals collected during the sleep study. Other signals collected during the sleep study may include respiratory signals, limb movement signals, electrocardiogram (ECG) signals, encephalogram (EEG) signals, nasal thermistor signals, flow signals, chest band movement signals, pleth signals, etc. In an embodiment, if a sleep apneaic event is identified and no respiratory signal is detected, the sleep apneaic event can be classified as central apnea. In contrast, if a sleep apneaic event is identified and an increase in respiratory effort is detected through respiratory signals received, the sleep apneaic event can be classified as obstructive apnea. In an embodiment, a detected blood pressure increase may be analyzed in view of an EEG signal in order to identify a sleep arousal. In an embodiment, variations in blood pressure during sleep can be analyzed in view of an EEG signal in order to identify different sleep stages (i.e., REM and non-REM sleep stages). In an embodiment, if an increase or decrease in blood pressure and a significant increase in limb movement signals are both detected, the increase or decrease in blood pressure may be considered to be an error and may be ignored.

In practice, one or more steps shown in processes 600 and 700 may be combined with other steps, performed in any suitable order, or removed. For example, the four sequences of steps performed in parallel in process 700 may instead be performed sequentially in any suitable order. In addition, the thresholds used in accordance with the disclosure may be the same for all subjects, may be the same for similar subjects, may be set for each subject based on an initial calibration or setting, or may dynamically change based on the detected blood pressure values.

The foregoing is merely illustrative of the principles of this disclosure and various modifications can be made by those skilled in the art without departing from the scope and spirit of the disclosure. For example, the present disclosure may be utilized during ordinary sleep as opposed to sleep studies. The above described embodiments are presented for purposes of illustration and not of limitation. The present disclosure also can take many forms other than those explicitly described herein. Accordingly, it is emphasized that the disclosure is not limited to the explicitly disclosed methods, systems, and apparatuses, but is intended to include variations to and modifications thereof which are within the spirit of the following claims.

What is claimed is:

1. A method for detecting sleep events, the method comprising:
    detecting, using at least one light sensor, at least one photoplethysmograph (PPG) signal based at least in part on receiving light that passed through blood perfused tissue;
    calculating, using a continuous non-invasive blood pressure (CNIBP) monitor, blood pressure based at least in part on the at least one PPG signal;
    determining, using the CNIBP monitor, changes in the blood pressure;
    analyzing, using the CNIBP monitor, the changes in the blood pressure to identify an abrupt change in the blood pressure; and
    identifying, using the CNIBP monitor, a sleep event based at least in part on the identified abrupt change in the blood pressure, wherein the sleep event is selected from the group consisting of sleep arousal and steep apneic event.

2. The method of claim 1, wherein detecting the at least one PPG signal comprises:
    detecting a first PPG signal from a first location on a subject; and
    detecting a second PPG signal from a second location on a subject, wherein calculating the blood pressure comprises:
        detecting, using the CNIBP monitor, a first time associated with a first pulse in the first PPG signal;
        detecting, using the CNIBP monitor, a second time associated with a second pulse in the second PPG signal;
        determining, using the CNIBP monitor, a time difference between the first time and the second time; and
        calculating, using the CNIBP monitor, the blood pressure based at least in part on the time difference.

3. The method of claim 1, wherein detecting the at least one PPG signal comprises:
    detecting a first PPG signal from a first location on a subject; and
    identifying, using the CNIBP monitor, at least two characteristic points in the detected PPG signal,
    wherein calculating the blood pressure comprises:
        determining, using the CNIBP monitor, a time difference between two of the at least two characteristic points in the detected PPG signal; and
        calculating, using the CNIBP monitor, the blood pressure based at least in part on the determined time difference.

4. The method of claim 1, wherein detecting the at least one PPG signal comprises:

detecting a first PPG signal from a first location on a subject; and determining locations of pulses in the PPG signal, wherein calculating the blood pressure comprises:

determining, using the CNIBP monitor, an area under a portion of one of the pulses; and calculating, using the CNIBP monitor, the blood pressure based at least in part on the area.

5. The method of claim 1, wherein determining changes in the blood pressure comprises:

calculating, using the CNIBP monitor, a first blood pressure value associated with a first time;

calculating, using the CNIBP monitor, a second blood pressure value associated with a second time;

determining, using the CNIBP monitor, a blood pressure difference between the first blood pressure value and the second blood pressure value;

comparing, using the CNIBP monitor, the blood pressure difference to a pre-defined threshold value; and identifying, using the CNIBP monitor, a sleep event, in response to determining that the blood pressure difference is greater than the pre-defined threshold value.

6. The method of claim 1, wherein determining changes in the blood pressure comprises:

calculating, using the CNIBP monitor, a long-term average blood pressure value;

calculating, using the CNIBP monitor, a short-term average blood pressure value;

determining, using the CNIBP monitor, a blood pressure difference between the long-term average blood pressure value and the short-term average blood pressure value;

comparing, using the CNIBP monitor, the blood pressure difference to a pre-defined threshold value; and identifying, using the CNIBP monitor, a sleep event, in response to determining that the blood pressure difference is greater than the pre-defined threshold value.

7. The method of claim 1, wherein determining changes in the blood pressure comprises:

starting a counter using the CNIBP monitor;

calculating, using the CNIBP monitor, a first blood pressure value associated with a first time;

calculating, using the CNIBP monitor, a second blood pressure value associated with a second time;

determining, using the CNIBP monitor, a time difference between the first time and the second time;

determining, using the CNIBP monitor, a blood pressure difference between the first blood pressure value and the second blood pressure value;

calculating, using the CNIBP monitor, a ratio of the blood pressure difference to the time difference;

comparing the ratio to a first pre-defined threshold value; and identifying, using the CNIBP monitor, a sleep event, in response to determining that the ratio continues to be greater than the first pre-defined threshold value and that the counter is greater than a second pre-defined threshold value.

8. The method of claim 1, wherein determining changes in the blood pressure comprises:

detecting, using the CNIBP monitor, a first blood pressure value associated with a first time when the blood pressure begins to change significantly;

detecting, using the CNIBP monitor, a second blood pressure value associated with a second time when the blood pressure begins to stabilize;

determining, using the CNIBP monitor, a time difference between the first time and the second time;

determining, using the CNIBP monitor, a blood pressure difference between the first blood pressure value and the second blood pressure value;

comparing, using the CNIBP monitor, the time difference to a first predefined threshold value and the blood pressure difference to a second pre-defined threshold value; and identifying, using the CNIBP monitor, a sleep event, in response to determining that the first time is less than the first pre-defined threshold value and the blood pressure difference is greater than the second pre-defined threshold value.

9. A continuous non-invasive blood pressure (CNIBP) system for detecting sleep events comprising:

a light sensor capable of detecting at least one photoplethysmograph (PPG) signal based at least in part on receiving light that passed through blood perfused tissue; and a CNIBP monitor configured to:

calculate blood pressure based at least in part on the at least one PPG signal;

determine changes in the blood pressure;

analyze the changes in the blood pressure to identify an abrupt change in the blood pressure; and identify a sleep event based at least in part on the identified abrupt change in the blood pressure, wherein the sleep event is selected from the group consisting of sleep arousal and steep apneic event.

10. The system of claim 9, wherein the CNIBP monitor is further configured to:

detect a first PPG signal from a first location on a subject;

detect a second PPG signal from a second location on a subject;

detecting a first time associated with a first pulse in the first PPG signal;

detect a second time associated with a second pulse in the second PPG signal;

determining a time difference between the first time and the second time; and calculated the blood pressure based at least in part on the time difference.

11. The system of claim 9, wherein the CNIBP monitor is further configured to:

detect a first PPG signal from a first location on a subject;

identify at least two characteristic points in the detected PPG signal;

determined a time difference between two of the at least two characteristic points in the detected PPG signal; and calculate the blood pressure based at least in part on the determined time difference.

12. The system of claim 9, wherein the CNIBP monitor is further configured to:

detect a first PPG signal from a first location on a subject;

receive locations of pulses in the PPG signal;

determine an area under a portion of one of the pulses; and calculate the blood pressure based at least in part on the area.

13. The system of claim 9, wherein the processor is further capable of:

calculate a first blood pressure value associated with a first time;

calculate a second blood pressure value associated with a second time;

determine a blood pressure difference between the first blood pressure value and the second blood pressure value;

compare the blood pressure difference to a pre-defined threshold value; and identify a sleep event, in response to determining that the blood pressure difference is greater than the pre-defined threshold value.

14. The system of claim 9, wherein the CNIBP monitor is further configured to:

calculate a long-term average blood pressure value;

calculate a short-term average blood pressure value;

determine a blood pressure difference between the long-term average blood pressure value and the short-term average blood pressure value;

compare the blood pressure difference to a pre-defined threshold value; and identify a sleep event, in response to determining that the blood pressure difference is greater than the pre-defined threshold value.

15. The system of claim 9, wherein the CNIBP monitor is further configured to:

start a counter;

calculate a first blood pressure value associated with a first time;

calculate a second blood pressure value associated with a second time;

determine a time difference between the first time and the second time;

determine a blood pressure difference between the first blood pressure value and the second blood pressure value;

calculate a ratio of the blood pressure difference to the time difference;

compare the ratio to a first pre-defined threshold value; and identify a sleep event, in response to determining that the ratio continues to be greater than the first pre-defined threshold value and that the counter is greater than a second pre-defined threshold value.

16. The system of claim 9, wherein the CNIBP monitor is further configured to:

detect a first blood pressure value associated with a first time when the blood pressure begins to change significantly;

detect a second blood pressure value associated with a second time when the blood pressure begins to stabilize;

determine a time difference between the first time and the second time;

determine a blood pressure difference between the first blood pressure value and the second blood pressure value;

compare the time difference to a first predefined threshold value and the blood pressure difference to a second pre-defined threshold value; and identify a sleep event, in response to determining that the time difference is less than the first pre-defined threshold value and the blood pressure difference is greater than the second pre-defined threshold value.

17. The system of claim 9, wherein determining changes in the blood pressure comprises determining a first value associated with a first change in the blood pressure, and a second value associated with a second change in the blood pressure, and wherein analyzing the changes in the blood pressure comprises analyzing the first value and the second value.

* * * * *